United States Patent [19]

Bass

[11] Patent Number: 5,132,917

[45] Date of Patent: Jul. 21, 1992

[54] METHOD AND APPARATUS FOR THE COMBINED USE OF DUAL DENSITY MEASUREMENTS TO ACHIEVE A FAST AND ACCURATE DENSITY MEASUREMENT IN PNEUMATICALLY TRANSPORTED SOLIDS

[75] Inventor: Ronald M. Bass, Houston, Tex.

[73] Assignee: Shell Oil Company, Houston, Tex.

[21] Appl. No.: 513,130

[22] Filed: Apr. 23, 1990

[51] Int. Cl.[5] .................. G01F 1/00; G01F 25/00; B65G 51/08

[52] U.S. Cl. ..................... 364/510; 364/558; 406/10; 73/861.04

[58] Field of Search .............. 364/510, 558, 550; 406/10, 12, 14, 28, 30; 73/861.04, 61 R

[56] References Cited

U.S. PATENT DOCUMENTS

| | | | |
|---|---|---|---|
| 3,635,082 | 1/1972 | Prellwitz et al. | 73/194 M |
| 4,049,394 | 9/1977 | Gernhardt et al. | 48/62 R |
| 4,270,558 | 6/1981 | Forster et al. | 137/2 |
| 4,490,077 | 12/1984 | Shimada et al. | 406/14 |
| 4,683,759 | 8/1987 | Skarsvaag et al. | 73/861.04 |
| 4,739,647 | 4/1988 | Monticelli, Jr. | 73/861.04 X |
| 4,751,842 | 6/1988 | Ekrann et al. | 73/861.04 X |
| 4,780,834 | 10/1988 | Craemer et al. | 364/510 |
| 4,782,711 | 11/1988 | Pratt | 364/510 |
| 4,817,439 | 4/1989 | Arnaudeau et al. | 73/861.04 |
| 4,838,738 | 6/1989 | Salter et al. | 406/14 |
| 4,884,457 | 12/1989 | Hatton | 73/861.04 |
| 4,969,408 | 11/1990 | Archer et al. | 364/510 |

Primary Examiner—Joseph L. Dixon

[57] ABSTRACT

The suspension density of a pneumatically transported solid, such as coal, is obtained by using a combination of a radial gamma ray densitometer and a second, fast-response density meter. The combination is required to get the desired combination of accuracy and response time. The second measurement is used for its fast response time and may be used to control operating conditions of a gasifier. The slower, but more accurate, radial radiation measurement is used to recalibrate the second measurement approximately every 10 seconds and correct for drift thereof. The drift in the second measurement is sufficiently slow that high accuracy can be maintained by the recalibration technique.

2 Claims, 3 Drawing Sheets

METHOD AND APPARATUS FOR THE COMBINED USE OF DUAL DENSITY MEASUREMENTS TO ACHIEVE A FAST AND ACCURATE DENSITY MEASUREMENT IN PNEUMATICALLY TRANSPORTED SOLIDS

FIELD OF THE INVENTION

The invention relates to measuring and controlling mass flow rate in pneumatically transported solids and in particular to the use of one measurement to calibrate a second measurement and thereby achieve a fast and accurate measurement.

BACKGROUND OF THE INVENTION

Conventional systems for controlling the mass flow rate of fine materials, such as particulate coal, supplied as a fuel into, for example, a furnace such as a coal-fired boiler, generally employ load-cell-based, weight-rate measuring systems to control the gross mass flow rate of the coal to boilers. Such a system is described in the Shimada et al. U.S. Pat. No. 4,490,077. In U.S. Pat. No. 4,838,738 issued to Assignee herein on Jun. 13, 1989, the fast response of a mass flow rate-indicating device is combined with the longer term accuracies in changes in the total mass from weight cells to yield rapid and more accurate loss-in-weight measurements than conventional systems.

U.S. Pat. No. 3,635,082 to Prellwitz et al. describes the determination of mass flow from velocity and density measurements of a coal and gas stream using two capacitance transducers mounted a known distance apart in the supply line between a coal storage vessel and furnace. The measurement system described by this patent relies on large signal variations, i.e., large changes in flow density, including inducing a change in flow density by injecting a burst of compressed gas into the supply line to produce a marker gap to observe "slugs" of coal in a gas stream in an industrial process. Such a system would not be compatible with Assignee's coal gasification process which requires a uniform mass flow rate of coal introduced to the gasifier over periods of time of approximately 5 seconds.

Other conventional systems control the mass flow rate by determining the mass flow rate indirectly via optical measurement of the coal concentration within a conduit leading to the furnace. Accurate control of mass flow by optical measurements, such as radiation absorption of infrared, UV or visible light, is limited to applications of low coal density suspensions, say less than 10 kg/cubic meter, since light must be transmitted through the coal mixture present in the conduit. Knowledge of the particle size distribution is also required. U.S. Pat. No. 4,049,394 to Gernhardt et al. describes a system for maintaining a predetermined volumetric ratio between fine-particle fuel and a gasification agent which are fed separately into a reactor. This system utilizes the principle of absorption of electromagnetic radiation by the fuel. First, the coal entrains gas as it passes from a storage vessel into a transport line. Additionally, the carrier gas is introduced to assist the coal in discharging from the vessel to the transport line en route to the gasifier. Since it is the total gas stream in the transport line in addition to other factors which govern which govern the mass flow rate, the invention described by this patent could not be used to control the mass flow rate of coal to a gasifier within the desired accuracy, say plus or minus 2 percent, operated with varying suspension densities of 100–800 kg/cubic meter having a variable coal particle size distribution, which are characteristic of the various coal types and various flow conditions required by the instant invention. Typical radiometric density measurements, although accurate, are too slow to ensure constant mass flow rates over short periods of time. Forster et al., U.S. Pat. No. 4,270,558, discloses a radiometric density measurement which compensates for the carrier gas. In Assignee's co-pending application Ser. No. 098,179 filed Sep. 18, 1987, the suspension density and mass flow rate of a particulate solids and gas mixture transported to a reactor is controlled by using a radiation source and detector. The suspension density is measured and compared to a preselected value. The result is converted to a control signal which may be used to control venting from the vessel, and/or the amount of aeration gas supplied to the lower portion of the vessel in order to maintain the suspension density at the preselected value and provide a constant mass flow rate. However, such systems do not disclose rapid manual or automatic on-line recalibration of mass flow rate controlling systems within a few seconds to accommodate changing operating conditions as required by the present invention. The present invention is directed to overcoming these problems in the prior art.

Applicant is not aware of any prior art which, in his judgment as one skilled in this particular art, would anticipates or render obvious the present invention. However, for the purpose of fully developing the background of this invention, and establishing the state of requisite art, the following art is set forth: U.S. Pat. Nos. 3,635,082; 4,490,077; 4,049,394; 4,838,738 and 4,270,558.

SUMMARY OF THE INVENTION

The primary purpose of the present invention relates to controlling, on a fast time scale, the mass flow rate of a solids and gas mixture to a reactor. In particular, this invention relates to controlling the mass flow rate of a particulate solid coal and gas mixture to a pressurized gasifier.

The invention combines the use of two separate density measurements to achieve a fast and accurate, gas-compensated coal density measurement in pneumatically transported solids flow. A gamma radiation density measurement may be taken across a diameter of a straight section of vertical pipe. This greatly limits the path length and therefore increases the measurement time required to achieve acceptable accuracy to perhaps 10 seconds. The improvement of the present invention uses a second density measurement to obtain a fast (but less accurate) response, and recalibrates it once a minute or more often with the slower, but more accurate, radiation measurement. This second measurement is used to control the mass flow rate of the system. The drift in the second measurement is sufficiently slow that high accuracy can be maintained by recalibrating at time intervals compatible with the measurement requirements of the radiation measurement. Thus, in the present invention, mass flow is determined from velocity and density measurements which are corrected for the density contribution of the transport gas. Velocity is determined from cross correlation of capacitance sensor signals. Density of the transport gas plus the solids is determined by a gamma ray densitometer supplemented with a second density measurement for faster response.

The second density measurement may be any one of the following: A fast but inaccurate radiation measurement may be obtained by measuring in a large radius curve or a "z" section so that the radiation can pass through a longer path in the transported material. In the present application, a segmented curve is used yielding a response time of approximately one second. In this geometry, the calibration is variable because the particles may redistribute themselves spatially in the curved or "z" section due to variations in velocity or particle size distribution. This results in a fast, but inaccurate, measurement. A fast density measurement may also be determined from the differential pressure along the pipe. This is obtained, for example, by solving the following equation for the coal suspension density, rc:

$$dp = f[(rg \times vg^2) + (rc \times vc^2)] + (rg \times g) + (rc \times g)$$

in vertical flow, or $$dp = f[(rg \times vg^2) + (rc \times vc^2)]$$

in horizontal flow, where
dp = differential pressure
f = friction factor
rg = gas density
vg = gas velocity
rc = coal suspension density
vc = coal velocity
g = gravitational acceleration All of these parameters, except solids density, rc, can be determined by direct measurement or by estimation from averaged data. For this method, the friction factor may vary due to variation in particle size distribution or physical makeup, so a continual recalibration is required. Measurement of differential pressure and other parameters in this equation requires less than one second. In electrically nonconducting materials, a capacitance density meter may be used for the second measurement. A capacitance density measurement is very fast but is susceptible to variation in suspension dielectric constant and temperature, especially if moisture is present. Coal, for example, will coat the inner lining of the capacitance sensor and, since it has a sufficiently high electrical conductivity, will effectively divert electric field lines around the suspended coal so that the density of flowing coal cannot be sensed.

Preferably, such an apparatus for the present invention includes:

(1) a gamma densitometer to accurately measure total mass density of the solids and the transport gas, (2) a second density measurement to rapidly measure the density of the solids, (3) transport gas pressure and temperature sensors, for obtaining the density of the transport gas, (4) an integrating computer to calculate the solids density (compensated for the transport gas) to obtain a corrected density of (1), and (5) means for calibrating the second density reading of (2) with the corrected gamma density reading of (4).

The fast, gas-compensated density reading can then be fed to a commercial mass flow meter which will measure velocity by cross correlation and calculate the mass flow required for gasifier control.

Preferably, a method for controlling the mass flow rate of solids to a reactor includes:

(1) accurately measuring total gamma density and correcting the reading for gas content by calculating gas density from pressure and temperature measurements averaged over the measurement time required for said accurate measurement in order to obtain a corrected gamma density measurement;

(2) calculating the coal volume fraction;

(3) obtaining a second density reading;

(4) calibrating the second density reading by:

a. calculating the average reading of the second densitometer over the last averaging period for the gamma densitometer and calibrating this reading to equal $f_{coal}r_{coal}$ where $f_{coal}$ = volume fraction of coal in the pipe and $r_{coal}$ = coal density; and b. scaling the second densitometer readings accordingly until they are updated by the next corrected gamma density reading from (1);

(5) controlling mass flow rate by adjusting operating conditions of the gasifier utilizing the calibrated density reading of step (4).

The various features of novelty which characterize the invention are pointed out with particularity in the claims forming a part of this disclosure. For a better understanding of this invention, its operating advantages and specific objects obtained by its uses, reference may be made to the accompanying drawings and descriptive matter in which there are illustrated preferred embodiments of the invention.

DESCRIPTION OF A PREFERRED EMBODIMENT

Figure 1:
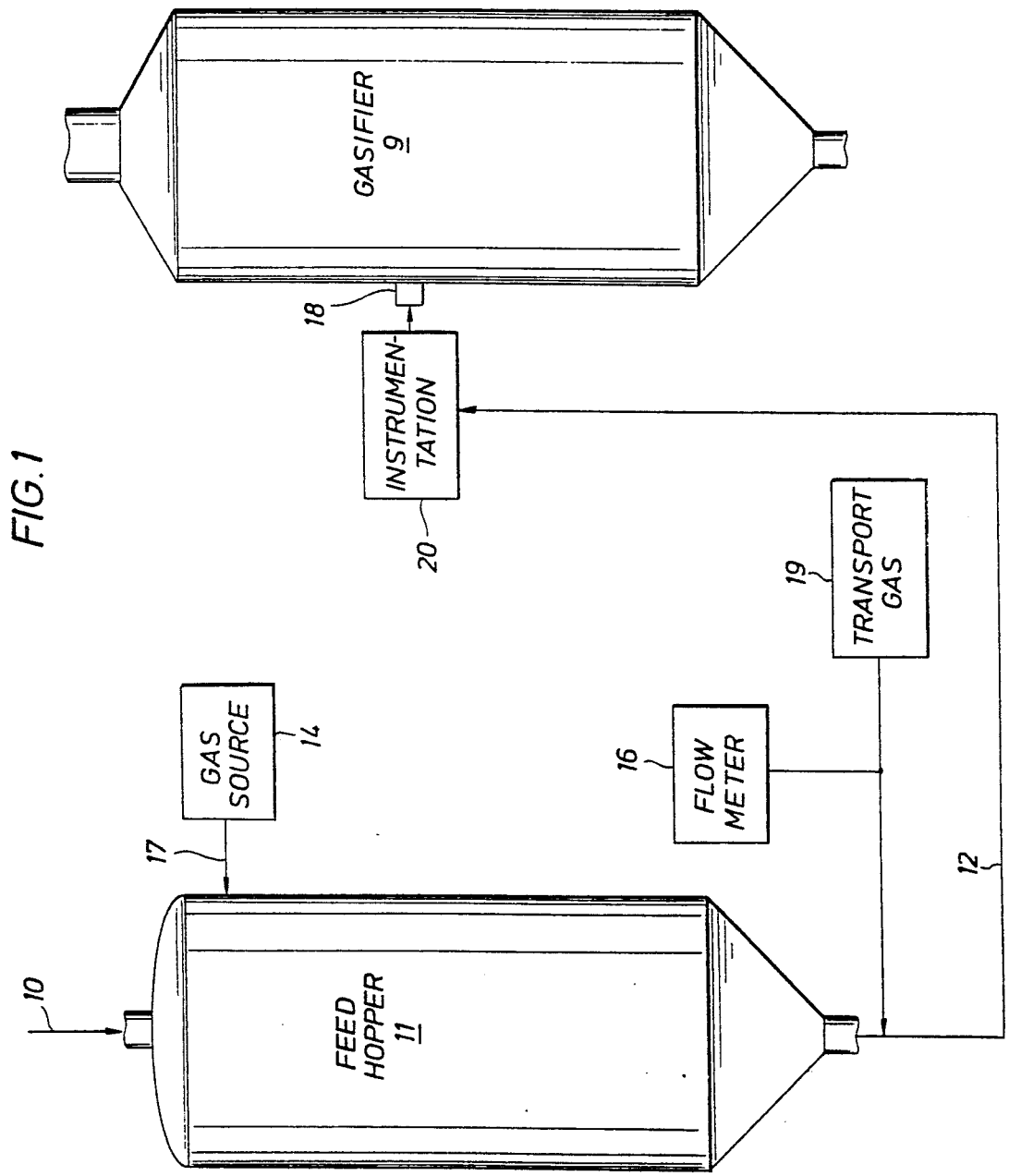
FIG. 1 illustrates a preferred embodiment of the invention.

Generation of synthesis gas (syngas) occurs by partially combusting organic or carbonaceous fuel, such as coal, at relatively high temperatures in the range of 800°-2000° C. and at a pressure range of from about 1-200 bar in the presence of oxygen or oxygen-containing gases in a gasifier. Oxygen-containing gases include air, oxygen enriched air, and oxygen optionally diluted with steam, carbon dioxide and/or nitrogen.

In the present invention, the fuel and gas mixture is discharged from a feed vessel apparatus, preferably having multiple outlets, each outlet being in communication with at least one burner associated with the gasifier. Typically, a gasifier will have four burners in diametrically opposing positions. Generally, the burners have their discharge ends positioned to introduce the resulting flame and the agent of combustion into the gasifier.

Of particular importance in the manufacture of synthesis gas is the uniform manner in which the particulate fuel is introduced to the burners within the gasifier and, in particular, the uniform mass flow rate of the fuel. Fluctuations of coal mass flow rate to burners within a coal gasification reactor, hereinafter referred to as a gasifier, are detrimental to the gasifier's performance. For example, fluctuations of the coal mass flow rate can cause inefficient combustion of fuel within the gasifier, i.e. zones of underheating generated next to zones of overheating in the gasifier. As a result, in the zones of underheating the fuel is not optimally gasified and in zones of overheating the fuel is completely converted into less valuable products, viz. carbon dioxide and water vapor. Additionally, damaging heat fluxes to the burner face can cause thermal stresses possibly resulting in shorter burner life. Furthermore, local high temperatures in the gasifier could damage the refractory lining which is normally arranged at the inner surface of the gasifier wall.

Based on the reasons identified above, maintaining a uniform mass flow rate of a coal and gas mixture to a gasifier is essential to effectively operating a gasifier. Since the residence time of coal in a gasifier can be 5 seconds or less, the coal mass flow rate should preferably be constant over periods of this order and preferably over longer periods to maintain constant local conditions.

As previously noted, measurement and automatic on-line control and recalibration of coal mass flow rate to the burners of a gasifier by conventional means, such as weight cells, or a single radiometric density measurement are too slow (or inaccurate) to ensure a constant mass flow rate to the burner of a gasifier over the time periods stated above. Similarly, other systems for controlling the mass flow rate by determining the mass flow rate indirectly via optical measurement of the coal concentration within a conduit leading to the furnace are limited to applications of the low coal density suspensions. Furthermore, the present method and apparatus disclosed herein for determining the mass velocity of the coal, allows the flexibility of operating the process at varying, and higher, suspension densities, say 100-800 kg/cubic meter, and at varying moisture contents of coal, which are characteristic of different coal types.

In Assignee's coal gasification process, coal is transported pneumatically by a suitable gas, preferably nitrogen or synthesis gas, in a small diameter (say 15 mm) pipe. A measurement of coal mass flow is needed to control the operation of the gasifier and is currently determined as follows:

(1) velocity is determined by cross correlation of signals from two closely spaced velocity sensors;
(2) flow density (pounds of coal per unit pipe volume) is measured by a single radiation measurement; and
(3) mass flow rate is computed by multiplying the coal flow density times the velocity times the pipe cross sectional area.

This system is not adequate for the above-noted reasons and improvement is required.

A radiation measurement may be obtained by injecting a beam of gamma rays through the pipe and measuring the degree of attenuation of the beam as it emerges from the pipe and impinges on a radiation detector. The more coal in the pipe, the greater the attenuation of the beam. Since this technique is sensitive to all mass present in the pipe, it must be corrected for the transport gas to give a net coal density.

The time required to get an accurate radiation measurement decreases with increasing path length in the mass to be measured. The desired accuracy response is about 0.5% for a one-second measurement. To get a sufficiently long path in the small diameter pipe, two 45-degree transitions may be introduced in the pipe in going from vertical transport (from the ground to the burner level of the gasifier) to horizontal transport into the burner. The transition is actually accomplished through a gradual curve in order to avoid excessive erosion of the pipe and the curved sections are necessarily included in the radiation measurements. This radiation density measurement is sensitive to velocity and particle size because of spatial redistribution of the solids within, and caused by, the curved measurement sections.

The curved pipe gamma ray densitometer installation has a longer path length and therefore gives a faster response time, for a given accuracy, than a radial installation across a straight section of the same pipe. The curved section may, as noted, induce nonuniform solids distribution that may vary with particle velocity or particle size distribution. If so, the gamma densitometer may be sensitive to changes in the solids distribution, i.e., inaccurate. Additionally, significant erosion may be observed in the curved tubes and can cause a negative offset in the densitometer calibration. Particle size distribution is normally stable for a given coal. The effect of velocity and density on densitometer calibration can be readily determined by running a series of velocities and densities through the densitometer. In these tests, a weigh cell is used to determine the true mass flow rate and the velocity is measured with the capacitance cross correlator. From these measurements the true suspension density is readily calculated and a correction factor is determined for the density indicated by the gamma densitometer.

A radial gamma densitometer installation, with its short path length, requires a much longer integration time for comparable accuracy than the curved pipe installation. The time required for an accurate measurement from the radial gamma densitometer is too slow to satisfy ideal control requirements. A second (curved) densitometer is therefore used for fast response, while the radial gamma densitometer is used for frequent recalibration (e.g., every 10 seconds) of the second densitometer. The calibrated second signal is then used to control gasifier operation for constant mass flow rate.

An advantage of the present invention is accurately controlling the mass flow rate of a coal and gas mixture to a gasifier having a residence time of five seconds or less and thereby preventing zones of underheating and overheating within the reactor.

Another advantage of the present invention is protection of the burners and refractory lining within the gasifier due to the prevention of zones of underheating and overheating.

An additional advantage of the present invention is more efficient conversion of solid fuel in the production of synthesis gas.

A further advantage of the present invention is the capability to directly measure the mass velocity of the coal, and thereby allow the flexibility of operating the process at varying, and higher, suspension densities, say 100-800 kg/cubic meter and at varying moisture contents of coal, which are characteristic of different coal types.

Although the invention is described hereinafter primarily with reference to particulate coal, the method and apparatus according to the invention are also suitable for catalysts and other finely divided reactive solids which could be partially combusted, such as lignite, anthracite, bituminous, brown coal, soot, petroleum coke, shale, tar sands and the like. Preferably, the size of solid carbonaceous fuel is such that 90 percent by weight of the fuel has a particle size smaller than No. 100 mesh (A.S.T.M.).

Having thus generally described the apparatus and method of the present invention, as well as its numerous advantages over the art, the following is a more detailed description thereof, given in accordance with specific reference to the drawings. However, the drawings are of process flow type in which auxiliary equipment, such as pumps, compressors, cleaning devices, etc., are not shown. All values are merely exemplary or calculated.

Referring to FIG. 1 of the drawings, an apparatus and method for controlling mass flow rate of a solids and gas mixture to a gasifier 9 operated at elevated pressures, say up to approximately 200 bar, generally includes feeding the mixture from a container (not shown), such as a bunker or silo, through a supply line 10 into a pressurized vessel, shown illustratively as a feed hopper 11, operated typically at pressures of 3–120 bar. A differential pressure of 2–20 bar between the hopper 11 and the gasifier 9 is maintained, preferably by injecting gas into an upper portion of the hopper 11 via line 17 from a pressurized gas source 14, to prevent flashback or ingress of synthesis gas into the hopper 11. The differential pressure is monitored and maintained by a pressure gauge and controller/control valve (not shown). A transport gas, such as nitrogen or synthesis gas, is supplied from source 19 to maintain coal flow through conduit 12 to the burners 18 of the gasifier 9. The rate of injecting transport gas is determined by a flow indicator 16. Near the burner 18 is located the instrumentation 20 of the present invention.

Figure 2:
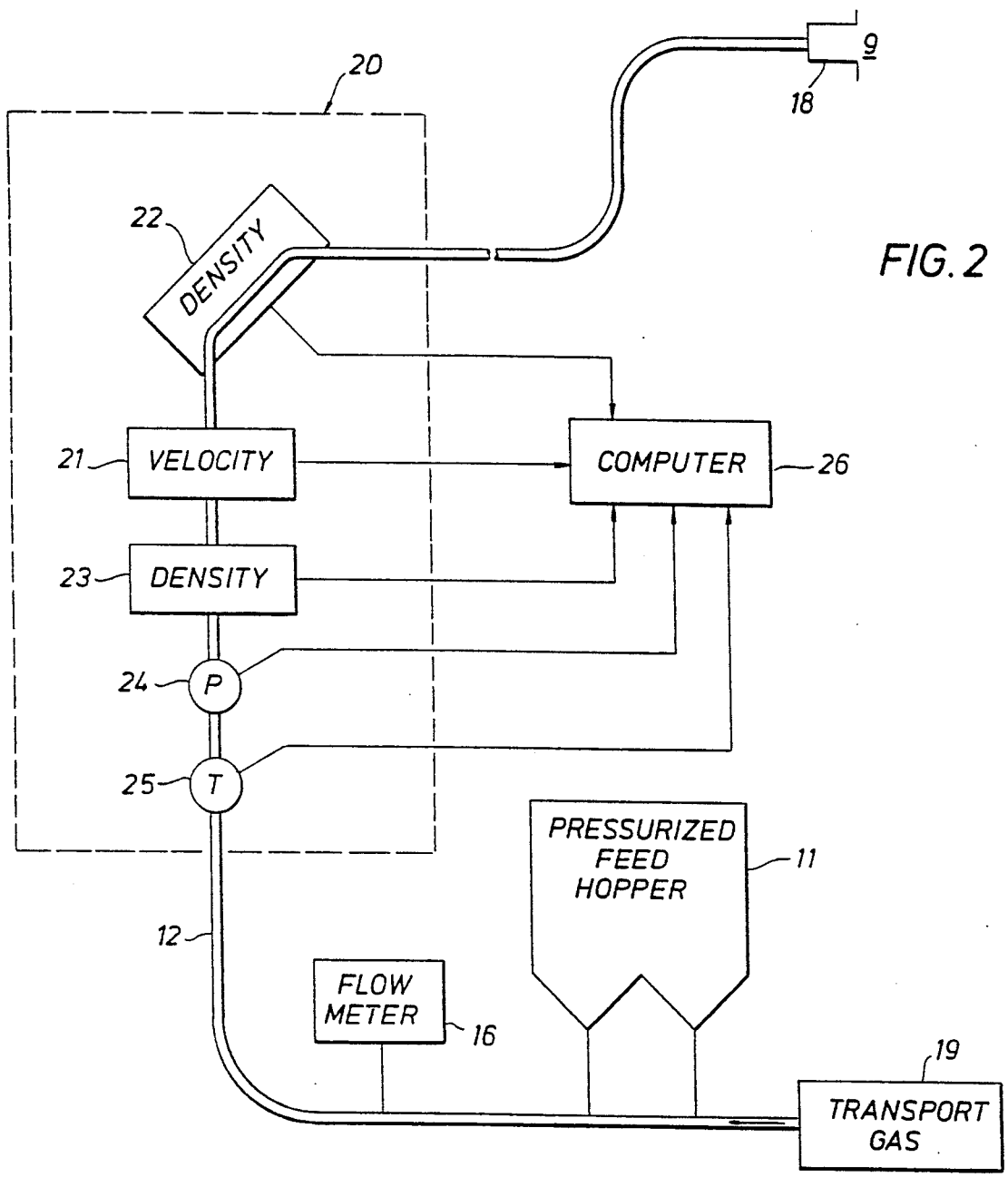
FIG. 2 is a block diagram of the preferred embodiment with instrumentation and computer interface.

Referring now to FIG. 2, which is a generalized schematic with the instrumentation being shown generally at 20, the particulate coal (having a known density) exits pressurized feed hopper 11 and is entrained in the transport gas 19, preferably nitrogen, and transported through conduit 12 to a burner 18 of gasifier 9. Prior to entering the burner 18, the particulate coal passes through a velocity sensor 21, a slow but accurate density meter 23 and a fast but inaccurate gamma radiation density meter 22. Additionally, pressure 24 and temperature 25 transducers are used, all to be subsequently described. All measurement signals are fed into computer 26. The slow density meter 23 may be, for example, a radial gamma densitometer.

Figure 3:
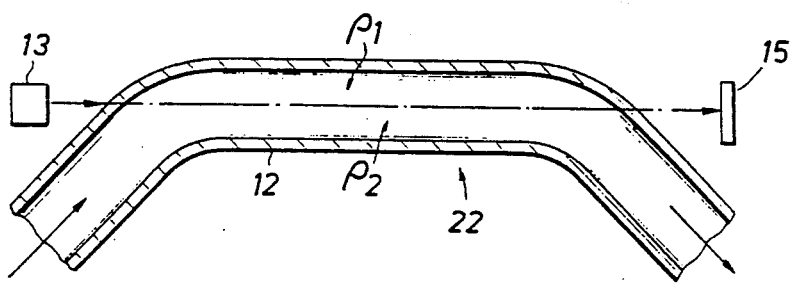
FIG. 3 is an enlargement of the instrumentation required for a fast gamma densitometer measurement.

For purposes of illustration, the invention will be described using a curved section of conduit 12 for the fast radiation density measurement by gamma ray densitometer 22 and a straight section of conduit is used for the slower, but more accurate, radial gamma ray densitometer 23. FIG. 3 is an enlargement of the curved section of conduit 12 through which particulates flow past gamma densitometer 22 to the gasifier 9. A gamma radiation source 13 is positioned so as to direct gamma radiation along the center of the conduit 12 where it is received by radiation detector 15 for determining the absolute density standard. Radiation from source 13 which is detected by the detector 15 is attenuated by the conduit 12 and by the particulate matter (and gas) flowing therethrough. Because of the curved conduit 12, the particulates flowing therethrough will normally assume a two-phase flow having densities $\rho_1$ and $\rho_2$ where $\rho_1$ is greater than $\rho_2$. For very low and very high densities, $\rho_1$ is approximately equal to $\rho_2$, i.e., approximately single-phase flow. For intermediate densities, excessive transport gas would be introduced (thereby diluting the heating value of the syngas) and the gamma densitometer 22 is less accurate; therefore, the high density method and apparatus of Assignee is required. The radiation source 13 may be, for example, a Model 5204 Source Head manufactured by Texas Nuclear having a 1000 mCi, Cesium 137 source. For a small diameter (say 15 mm) conduit 12, the source may be on the order of 100 mCi. The detector 15 may be a Type SCN-SGD Gamma-Ray Detector manufactured by Texas Nuclear. Where a straight section of conduit 12 is used, as with radial densitometer 23, the source 13 and detector 15 are located in diametrically opposing positions.

Figure 4:
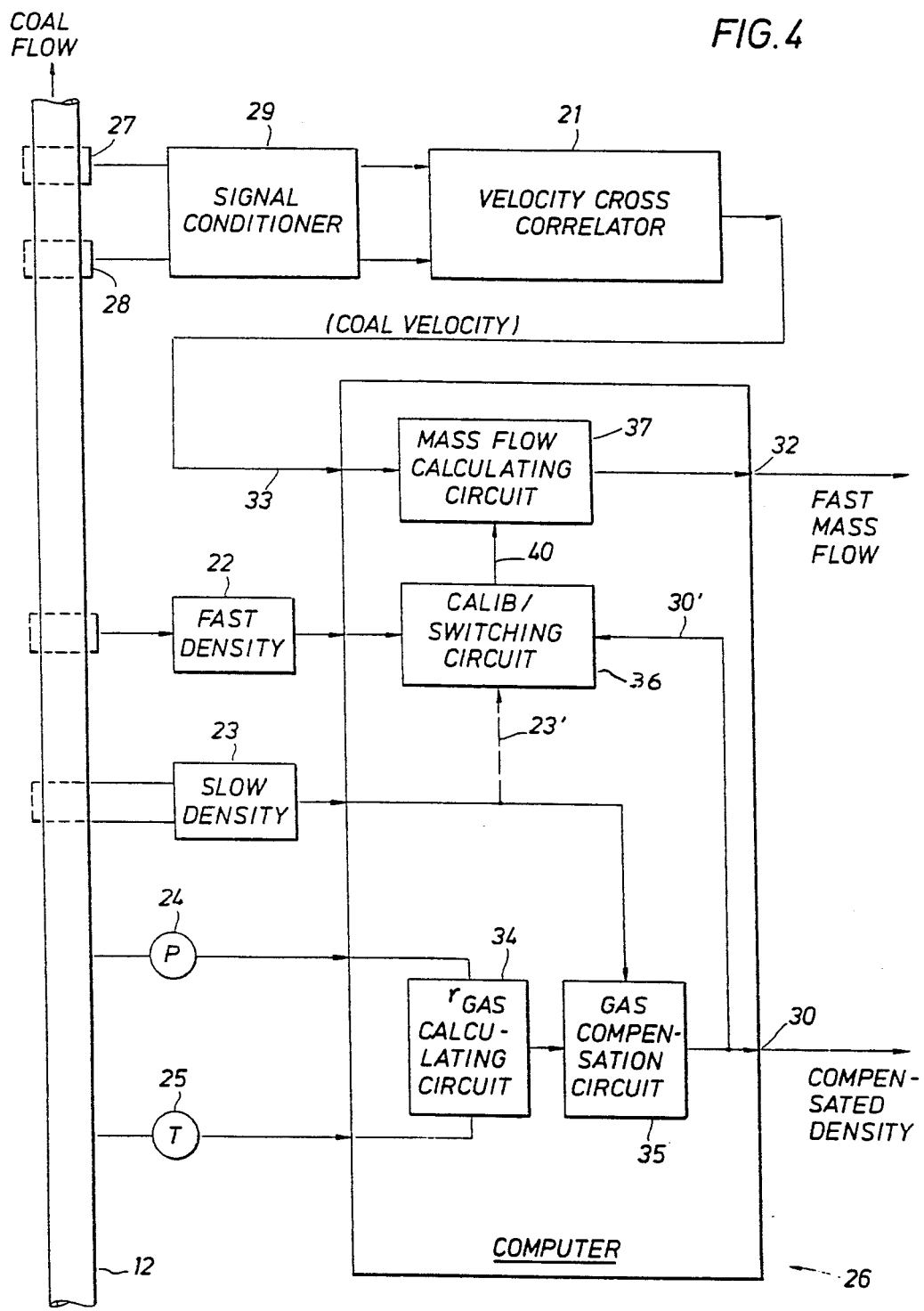
FIG. 4 is a schematic diagram of the system instrumentation integrated with a computer.

Referring now to FIG. 4, since the radiation measurement from radial densitometer 23 is acceptably accurate, but has a slow response time, a second density meter 22 is used to obtain a density measurement with a fast response time. The density meter 22 may be (as noted) a gamma density meter or any other direct or indirect fast method of measuring density. For electrically non-conducting materials, a densitometer 22 such as an Endress and Hauser Capacitance Densitometer Model No. DMC 170 may be used. Since the density measurement varies with time, the accurate, and time-averaged, radiation measurement of the radial gamma ray densitometer 23 is used (as subsequently described) to continually recalibrate the second (fast) density measurement 22 approximately every 10 seconds. The calibrated measurement of fast density meter 22 is transmitted via conductor 40 to mass flow calculating circuit 37 where it is combined with coal velocity 33 to obtain the mass flow 32 which is used to control the operating conditions of the gasifier. Coal velocity 33 may be determined by velocity cross correlator 21, which may be an Endress and Hauser system Model No. DMK 170 using capacitance sensors 27, 28 and a signal conditioner 29. The required sensor spacing depends on the nature of the flow. Pressure and temperature are obtained by appropriate sensors 24 and 25, respectively. An integrating computer 26, such as the Fischer and Porter CHAMELEON, Microcomputer Mark II, may be used to integrate the velocity, density, pressure and temperature signals to determine total mass flow, corrected for transport gas contribution, to obtain $f_{coal}$ the volume fraction of coal alone.

Thus, in the present invention, if we let:

$r_{coal}$ = coal density $r_{gas}$ = transport gas density (determined in the usual way from pressure and temperature measurements)

$r_{gamma}$ = total (uncompensated) flowing density measured by the gamma densitometer $f_{coal}$ = volume fraction of coal in the pipe $f_{gas}$ = volume fraction of gas in the pipe = $1 - f_{coal}$ A = pipe cross sectional area, and $v_{coal}$ = average coal velocity in pipe, measured by capacitance cross correlation then $$\text{coal mass flow} = r_{coal} v_{coal} A f_{coal} \tag{1}$$

and since $$r_{gamma} = f_{coal} r_{coal} + f_{gas} r_{gas} \tag{2}$$

$$= f_{coal} r_{coal} + (1 - f_{coal}) r_{gas} \tag{3}$$

then $$\text{coal volume fraction} = f_{coal} = \frac{r_{gamma} - r_{gas}}{r_{coal} - r_{gas}}.$$

which is corrected for the density of the gas.

FIG. 4 shows a schematic of the system instrumentation 20 integrated with a computer 26. Particulate coal flows through conduit 12 toward the gasifier 9 and the following measurements are obtained: temperature is obtained by temperature sensor 25; pressure by pressure sensor 24; slow density by radial gamma ray densitometer 23 (which measurement includes coal and the transport gas); fast density by curved gamma densitometer 22; and velocity by velocity sensors 27, 28, signal conditioner 29 and velocity cross correlator 21. All five resulting signals are input to the computer 26. The pressure 24 and temperature 25 measurements are combined to obtain the transport gas density, $r_{gas}$, in $r_{gas}$ calculating circuit 34 which, in turn, is combined with the radial gamma density measurement 23 ($r_{gamma}$) in gas compensation circuit 35 to obtain a compensated gamma density measurement (i.e., $f_{coal}r_{coal}$) which is shown as output 30 of computer 26. Velocity cross correlator 21 receives inputs from two capacitance sensors 27, 28 via signal conditioner 29 and computes the average coal velocity $v_{coal}$ 33 in the conduit 12. In operation, the fast but inaccurate density measurement obtained by curved gamma densitometer 22 is combined via conductor 40 with the velocity measurement $v_{coal}$ 33 in mass flow calculating circuit 37 to obtain the mass flow (fast but inaccurate) at terminal 32 of computer 26. The output at terminal 32 is used to control gasifier operation for maintaining a constant mass flow rate. The signal from fast density measurement 22 is corrected periodically (every 10 seconds, for example) in calibration/switching circuit 36 by compensated density signal 30 via conductor 30' to obtain a corrected density measurement on conductor 40 that is accurate, fast and compensated for transport gas density. In practice, the transport gas accounts for only about 5% or less of the suspension density, especially at high suspension densities. Thus the second densitometer signal 22 could be calibrated directly with the uncompensated gamma density $r_{gamma}$ signal 23 (via dashed line 23') to give a fast, calibrated but uncompensated, density measurement on conductor 40. This signal could then be combined with the velocity measurement $V_{coal}$ 33 and would result in only a small error in the mass flow signal at terminal 32. The calibrated density reading on conductor 40 is obtained in the following manner:

Let
$\rho_s$ = compensated density 30 (or slow density 23);
$\overline{\rho_s}$ = time averaged (say 30 seconds) slow density measurement:
$\rho_F$ = instantaneous (fast) density measurement 22; and
$\overline{\rho_F}$ = time averaged fast density measurement;
then the corrected instantaneous density =

$$\hat{\rho} = \frac{\rho_F}{\overline{\rho_F}} \overline{\rho_s} \text{ where}$$

$\hat{\rho}$ is the corrected density measurement on conductor 40.

The calibrated (and, if required, compensated) density measurement on conductor 40 is combined with the velocity measurement $v_{coal}$ 33 to obtain a corrected mass flow measurement at terminal 32 which can then be used (e.g.) to control the flow of particulate coal from hopper 11 to maintain a desired mass flow rate which is essentially constant over a long period of time.

Many variations of this procedure are possible, including use of multiple gamma density averages to predict the drift in the fast density readings.

The foregoing description of the invention is merely intended to be explanatory thereof, and various changes in the details of the described method and apparatus may be made within the scope of the appended claims without departing from the spirit of the invention.

What is claimed is:

1. A system for determining the mass flow rate of a solid transported through a conduit by a gaseous transporting medium comprising:
   first gamma densitometer means for obtaining a first total mass density measurement of said solid and said transporting medium flowing in said conduit said measurement being taken on a diameter of said conduit;
   second gamma densitometer means for obtaining a second total mass density measurement of said solid and said transporting medium flowing in said conduit, said second densitometer being located on a curved portion of said conduit such that radiation is directed along the lineal axis of said conduit;
   pressure and temperature sensors in said conduit for measuring the pressure and temperature of said transporting medium;
   means connected to said sensors for calculating the density of said transporting medium from said pressure and temperature measurements;
   an integrating computer for receiving said density measurements and calculating the solids density compensated for the density of said transporting medium to obtain a compensated density measurement;
   means for periodically calibrating said second densitometer with said compensated density measurement to obtain a calibrated density measurement;
   means for measuring the velocity of said solids flow; and
   computer means for calculating the mass flow rate of said solids from said velocity and said calibrated density measurements.

2. A method for controlling the mass flow rate to a gasifier of a solid pneumatically transported in a gaseous medium through a conduit to said gasifier comprising the steps of:
   measuring the total gamma density of said solid and said gaseous medium with a first gamma densitometer located on a diameter of said conduit;
   averaging said measurement over a predetermined period of time to obtain a total gamma density measurement;
   measuring the pressure and temperature of said gaseous medium;
   calculating the density of said gaseous medium;
   subtracting the density of said gaseous medium from said total gamma density measurement to obtain a compensated gamma density measurement;
   obtaining a second total gamma density measurement with a second gamma densitometer said second measurement being obtained on a curved portion of said conduit such that radiation is directed along the lineal axis of said conduit;
   calibrating said second densitometer by:
   (1) calculating the average reading of said second densitometer over the last predetermined averaging period for said first gamma density measurement and calibrating said average reading to equal said compensated gamma density measurement to obtain a calibrated reading;

(2) obtaining a corrected mass flow rate by scaling said second densitometer reading with said calibrated reading until said second densitometer reading is updated by the next compensated gamma density measurement; and controlling the mass flow rate of said solid to said gasifier by adjusting the mass flow rate of said gasifier with said corrected mass flow rate reading.

* * * * *